(12) United States Patent
Weikert et al.

(10) Patent No.: US 11,571,540 B2
(45) Date of Patent: Feb. 7, 2023

(54) RESPIRATORY VALVE APPARATUS AND RELATED METHOD

(71) Applicant: Innovation Lab, LLC, Newport Beach, CA (US)

(72) Inventors: Nicole Marie Weikert, Huntington Beach, CA (US); Harry Bayron, West Palm Beach, FL (US); Neil Winthrop, West Palm Beach, FL (US); Nikolai Poulsen, Irvine, CA (US)

(73) Assignee: Innovation Lab, LLC, La Palma, CA (US)

( * ) Notice: Subject to any disclaimer, the term of this patent is extended or adjusted under 35 U.S.C. 154(b) by 689 days.

(21) Appl. No.: 16/467,913

(22) PCT Filed: Dec. 6, 2017

(86) PCT No.: PCT/US2017/064917
§ 371 (c)(1),
(2) Date: Jun. 7, 2019

(87) PCT Pub. No.: WO2018/106808
PCT Pub. Date: Jun. 14, 2018

(65) Prior Publication Data
US 2019/0336718 A1 Nov. 7, 2019

Related U.S. Application Data

(60) Provisional application No. 62/431,301, filed on Dec. 7, 2016.

(51) Int. Cl.
*A61M 16/20* (2006.01)
*A61M 16/08* (2006.01)
(Continued)

(52) U.S. Cl.
CPC ........ *A61M 16/20* (2013.01); *A61M 16/0816* (2013.01); *A61M 39/223* (2013.01);
(Continued)

(58) Field of Classification Search
CPC .......... A61M 16/0078; A61M 16/0084; A61M 16/0463; A61M 16/0816; A61M 16/0833;
(Continued)

(56) References Cited

U.S. PATENT DOCUMENTS

| 4,416,273 A | 11/1983 | Grimes |
| 5,139,018 A | 8/1992 | Brodsky et al. |

(Continued)

FOREIGN PATENT DOCUMENTS

EP 1239907 B1 9/2007

*Primary Examiner* — Annette Dixon
(74) *Attorney, Agent, or Firm* — Mintz Levin Cohn Ferris Glovsky and Popeo, P.C.

(57) ABSTRACT

One aspect of the disclosure includes a respiratory valve apparatus. The respiratory valve apparatus may include: a housing having an inner chamber, an endotracheal tube connection port, a ventilator connection port, and a resuscitation bag connection port; and a piston assembly positioned within the inner chamber and including a piston having a first passageway and a second passageway through the piston, wherein the first passageway provides a first flow pathway between the endotracheal tube connection port and the ventilator or connection port when the piston is in a first position, and wherein the second passageway provides a second flow pathway between the endotracheal tube connection port and the resuscitation bag connection port when in a second position.

20 Claims, 11 Drawing Sheets

(51) Int. Cl.
*A61M 39/22* (2006.01)
*F16K 11/04* (2006.01)
A61M 16/00 (2006.01)
A61M 16/04 (2006.01)

(52) U.S. Cl.
CPC .......... *F16K 11/04* (2013.01); *A61M 16/0084* (2014.02); *A61M 16/04* (2013.01); *A61M 2039/226* (2013.01)

(58) Field of Classification Search
CPC .. A61M 16/0858; A61M 16/12; A61M 16/20; A61M 16/208; A61M 16/209; F16K 11/044; F16K 11/0716
See application file for complete search history.

(56) References Cited

U.S. PATENT DOCUMENTS

| | | | |
|---|---|---|---|
| 5,357,946 A | 10/1994 | Kee et al. | |
| 5,526,804 A | 6/1996 | Ottestad | |
| 5,746,199 A * | 5/1998 | Bayron | A61M 16/20 128/205.24 |
| 6,237,597 B1 | 5/2001 | Kovac | |
| 6,886,561 B2 * | 5/2005 | Bayron | F16K 11/0716 128/207.14 |
| D519,632 S | 4/2006 | Bayron et al. | |
| 7,207,332 B1 * | 4/2007 | Lugtigheid | A61M 16/0858 128/205.24 |
| 7,258,120 B2 | 8/2007 | Melker | |
| 8,656,915 B2 * | 2/2014 | Bayron | A61M 16/209 128/205.24 |
| 2006/0060199 A1 | 3/2006 | Lampotang et al. | |
| 2015/0320961 A1 | 11/2015 | Maguire | |

* cited by examiner

RESPIRATORY VALVE APPARATUS AND RELATED METHOD

CROSS-REFERENCE TO RELATED APPLICATIONS

This application is a national stage entry, filed under 35 U.S.C. § 371, of International Application No. PCT/2017/064917, filed on Dec. 6, 2017, and claims priority to U.S. Provisional Application No. 62/431,301 filed on Dec. 7, 2016, the entire contents of each are incorporated herein by reference in their entireties and for all purposes.

BACKGROUND

Respiratory support systems are commonly used to support the respiratory system of a critically ill patient for maintaining optimal blood oxygen levels, as well as optimal carbon dioxide levels and acid base balance. Typically, a prior art respiratory support system includes a tracheal tube, positioned either directly through the nose or mouth into the trachea of a patient. A multi-ported manifold is connected to the endotracheal tube at one port position, and a source of breathable gas is connected at a second port. The respiratory support system assists the patient in maintaining adequate blood oxygenation levels without overtaxing the patient's heart and lungs.

While a patient is attached to the respiratory support system, it is periodically necessary to aspirate fluids and or secretions from the patient's trachea and lungs. In the past, in order to accomplish aspiration and positive pressure ventilation, it was necessary to disassemble part of the respiratory support system, either by removing the ventilator manifold or by opening a port thereof and inserting a small diameter suction tube down the tracheal tube and into the patient's trachea and lungs. The fluid was then suctioned from the patient and the suction catheter was removed and the respiratory support system reassembled. However, due to the interruption of respiratory support during this procedure, a patient's blood oxygen can often drop and the carbon dioxide can change to unacceptable levels. Disassembly of the respiratory support system for suctioning and other noninvasive procedures, such as bronchoscopy, can expose the patient's lungs to possible contaminants in the environment thereby increasing the chances of acquiring ventilator associated pneumonia (VAP). Additionally, unless a sufficient positive end expiratory pressure (PEEP) level is maintained, then the lungs might collapse. This creates a dangerous condition for the patient because the lungs can be difficult, and sometimes impossible, to reinflate.

Patients may have fluid drawn from their lungs as often as six times a day and sometimes more, possibly over long periods of time. As such, a benefit can be achieved with a respiratory device that can minimize patient discomfort while allowing various procedures (e.g., bronchoscopies) and lung measurements to be taken, such as before weaning a patient off a ventilator. In addition, such a device could be widely used in treating pediatric patients, especially premature infants, as well as adults, who are subject to respiratory problems and may need frequent aspirations. As a result of the extremely large number of aspirations necessary on various patients in any period, it is important that the price of the respiratory device be as low as possible since vast numbers will be used. It is also important that the device be sufficiently inexpensive so that it may be discarded after a single use. Hence, it is desirable to simplify such devices and reduce the number of parts in order to reduce costs and increase reliability.

SUMMARY

One aspect of the disclosure includes a respiratory valve apparatus. The respiratory valve apparatus may include: a housing having an inner chamber, an endotracheal tube connection port, a ventilator connection port, and a resuscitation bag connection port; and a piston assembly positioned within the inner chamber and including a piston having a first passageway and a second passageway through the piston, wherein the first passageway provides a first flow pathway between the endotracheal tube connection port and the ventilator connection port when the piston is in a first position, and wherein the second passageway provides a second flow pathway between the endotracheal tube connection port and the resuscitation bag connection port when in a second position.

A second aspect of the disclosure includes method. The method may include: providing a respiratory valve apparatus including: a housing having an inner chamber, an endotracheal tube connection port, a ventilator connection port, and a resuscitation bag connection port; and a lever member disposed within the inner chamber, the lever member being biased in a first position thereby defining a first passageway between the endotracheal tube port and the ventilator connection port, and wherein the lever member is pivotable to a second position thereby defining a second passageway between the endotracheal tube port and the resuscitation bag connection port.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

Figure 1:
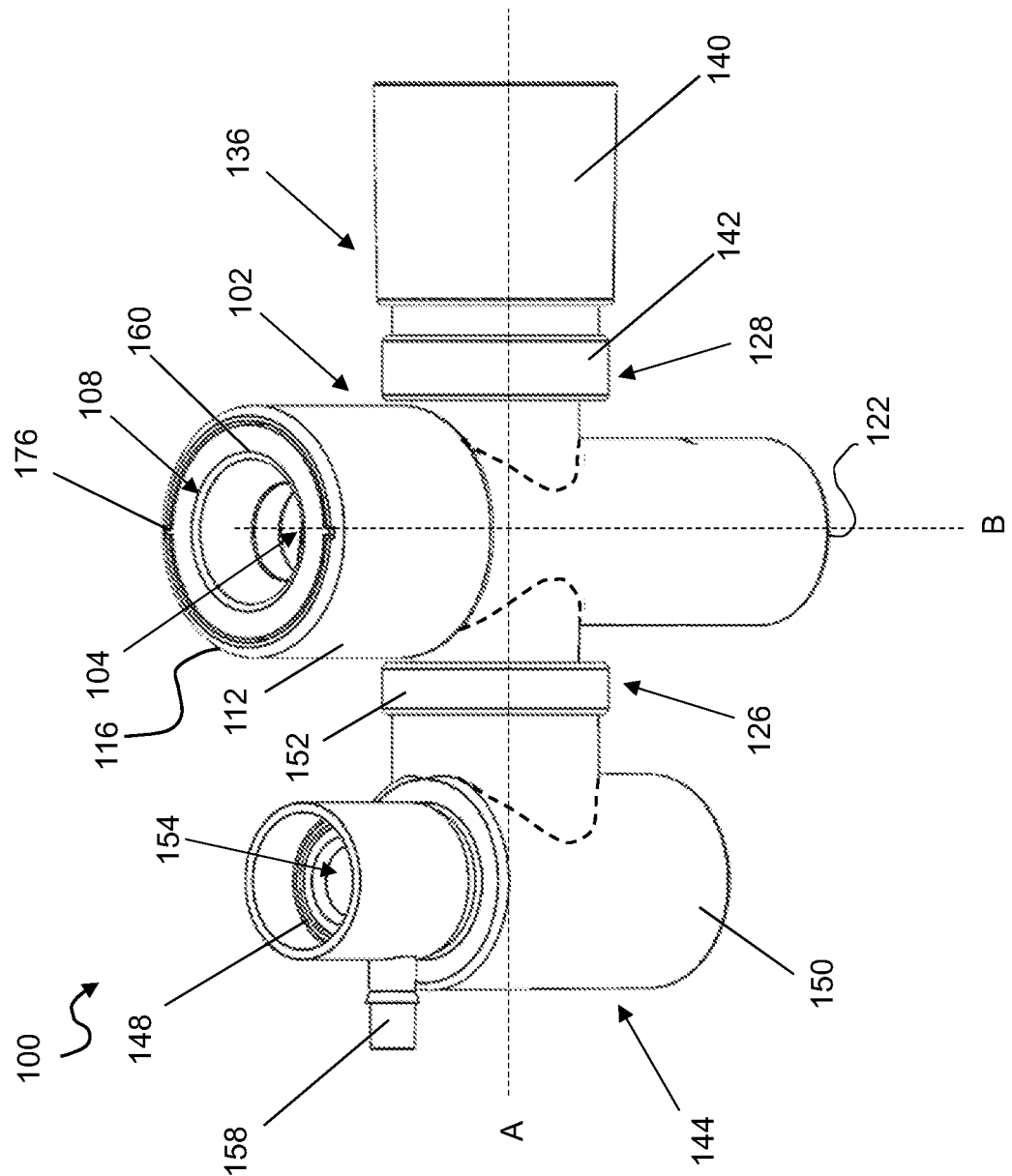
FIG. 1 shows a perspective side view of an embodiment of a respiratory valve apparatus described herein.

It is noted that the drawings of the subject matter are not necessarily to scale. The drawings are intended to depict only typical aspects of the subject matter, and therefore should not be considered as limiting the scope other disclosed subject matter. In the drawings like numbering represents elements between the drawings.

DETAILED DESCRIPTION

Described herein includes various embodiments of a respiratory valve apparatus including at least four ports (e.g., a ventilator connection port, a suction catheter port, an endotracheal tube port, and a resuscitation bag port) that enable a patient to be switched from mechanical to manual ventilation (e.g., using a resuscitation bag) without the need to open a ventilator circuit. This can reduce the risk of ventilator-acquired pneumonia and loss of positive-end expiratory pressure (PEEP) for the patient. The risk of the healthcare worker being exposed to any fluids contained within the ventilator system is also reduced or eliminated with the respiratory valve described herein.

The respiratory valve apparatus described herein provides improvements over other valves, including other respiratory valves. For example, the respiratory valve apparatus disclosed herein includes a piston configuration within the valve that allows for two alternate air pathways passing through the piston. In addition, the respiratory valve apparatus provides an improved transition between mechanical and manual ventilation. Furthermore, the respiratory valve apparatus provides reduced dead space within the valve. Such improvements (either alone or in combination) can assist with maintaining positive-end pressure in the patient and reduce the risk of the patient rebreathing $CO_2$ during ventilation.

In some embodiments, the respiratory valve apparatus can include the following features: at least four main ports (e.g., a ventilator connection port, a suction catheter port, an endotracheal tube port, and a resuscitation bag port); the ability to switch from mechanical ventilation to manual (e.g. via a resuscitation bag) without opening of the ventilation circuit; the ability to conduct lung measurement studies without opening the ventilator circuit; a piston mechanism within the respiratory valve apparatus that securely switches from a ventilator to a resuscitation bag as the resuscitation bag is placed on or in connection with the resuscitation bag port; a suction catheter port that is directly in-line with the patient and has a sealing member to allow for medical procedures (e.g., bronchoscopy, drug delivery) to be carried out without interference from ventilator airflow and minimal risk of contamination; an irrigation port positioned along the suction catheter port; swivel connectors along the valve apparatus can allow for ergonomic positioning of the valve regardless of which ports are in use.

Figure 2:
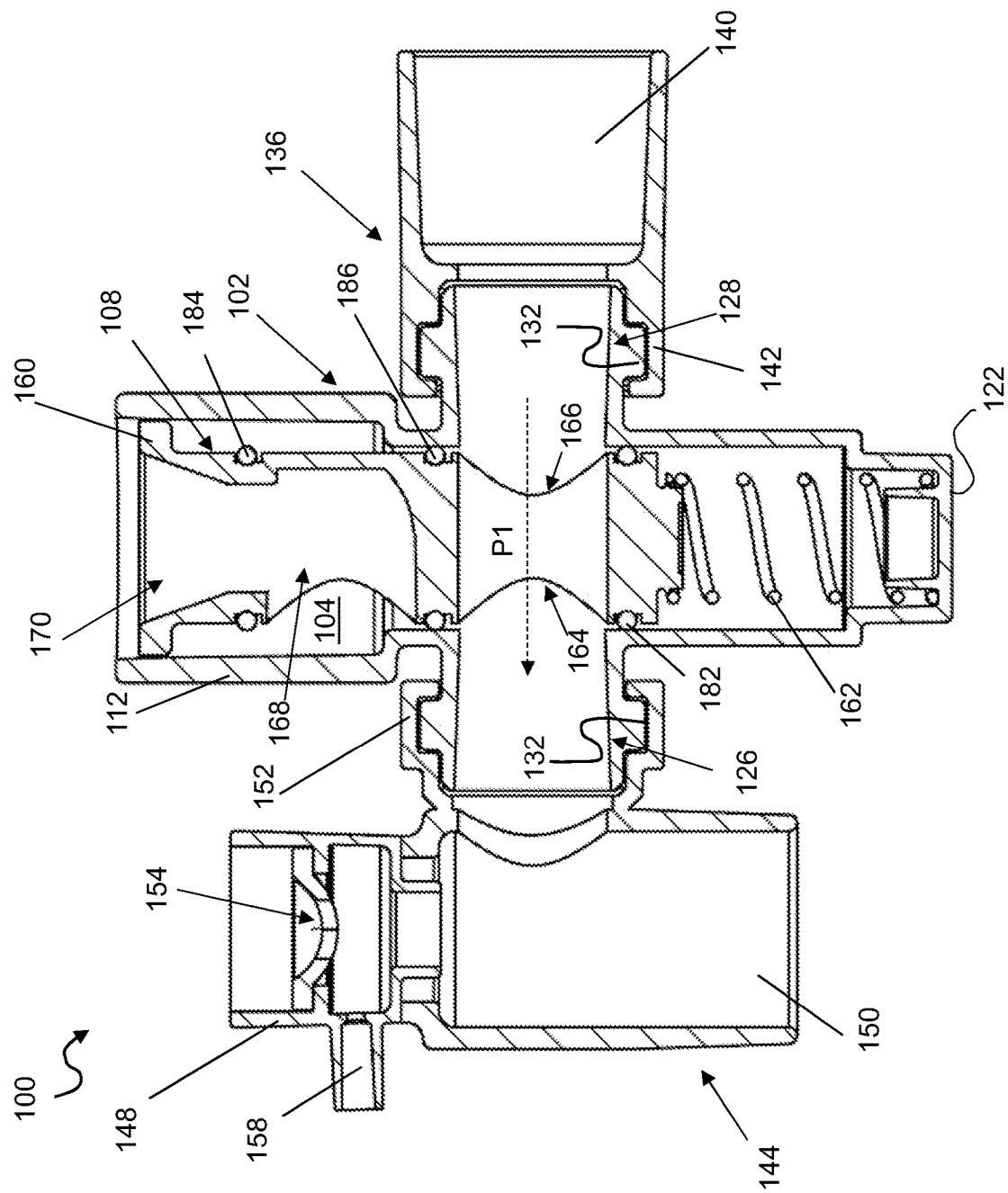
FIG. 2 shows a cross-section of the respiratory valve apparatus in a first configuration including a piston in a first position thereby creating a first fluid pathway between a patient and a ventilator.

Turning now to FIGS. 1-2, an embodiment of a respiratory valve apparatus 100 is shown. Respiratory valve apparatus 100 may include a housing 102 having an inner chamber 104 disposed therein. Housing 102 may be substantially t-shaped or x-shaped and may house a piston assembly 108 within inner chamber 104. As used herein, the terms "about," "substantially," "approximately," and variations thereof are intended to include the degree of error associated with measurement of the particular quantity based upon the equipment available at the time of filing the application. As will be described herein, piston assembly 108 may control air flow between one or more parts of respiratory valve apparatus 100. Housing 102 may also include a resuscitation bag connection port 112 on a first end 116 of housing 102. Resuscitation bag connection port 112 may be sized and shaped to accommodate a resuscitation bag (not shown) being engaged, connected, attached, joined, linked and/or fastened thereto. For example, resuscitation bag connection port 112 may be threaded or include rotation locking grooves for receiving and retaining the resuscitation bag. However, any conventional means may be used for receiving and retaining the resuscitation bag within or on resuscitation bag connection port 112. As described herein, a resuscitation bag can include a bag valve mask, manual resuscitator, and/or an ambu-bag, including various embodiments known in the art for using with assisting with respiration.

Housing 102 may include a closed, second end 122 opposite or substantially aligned with first end 116. As will be described herein, second end 122 may function as a spring seat or spring stop when a resuscitation bag is retained on or within resuscitation bag connection port 112. Housing 102 may also include a third end 126 opposing a fourth end 128 defining a line A normal to a line B defined by first and second ends 116, 122. Each of third end 126 and fourth end 128 may include a connection member 132. Connection members 132 may include, for example, a flange, rib, rim, void, swivel connector, female connection member and/or a male connection member for securing and/or retaining conduits thereto.

For example, respiratory valve apparatus 100 may also include a conduit 136 including a ventilator connection port 140 and a connection member 142. Connection member 142 may be disposed on an opposing end of conduit 136 from ventilator connection port 140. Connection member 142 may include any means for matingly engaging with connection member 132 of one of third end 126 or fourth end 128 of housing 102 such as, for example, a flange, rib, rim, void, a swivel connector, a female connection member, and/or a male connection member. For example, where connection member 132 includes a male connection member, connection member 142 may include a female connection member. Connection members 132, 142 may matingly engage, connect, attach, join, link and/or fasten such that conduit 136 is in fluid communication with housing 102. While conduit 136 is shown as being matingly engaged with fourth end 128 of housing 102, it is to be understood that conduit 136 may instead matingly engage with third end 126. Connection members 132, 142 may allow for ergonomic positioning of conduit 136 relative to housing 102 thereby aiding in the use of ventilator connection port 140 and resuscitation bag connection port 112. For example, connection members 132, 142 may engage such that connection members 132, 142 allow 360° rotation of conduit 136 to prevent kinking, twisting, or tangling of the artificial airway circuit. Ventilator connection port 140 may also be known as a respirator connection port, and may be sized and shaped to accommodate a respirator or ventilator (not shown) being engaged, connected, attached, joined, linked and/or fastened thereto. Ventilator connection port 140 may be threaded or include rotation locking grooves (not shown) for receiving and retaining the respirator or ventilator. However, any conventional means may be used for receiving and retaining the ventilator within or on ventilator connection port 140.

Respiratory valve apparatus 100 may also include a conduit 144 including an accessory port 148, an endotracheal tube connection port 150, and a connection member 152. Accessory port 148 may be sized and shaped for receiving any desirable medical accessory, e.g., a suction catheter (not shown), bronchoscope (not shown), or drug delivery catheter (not shown), etc., being engaged, connected, attached, joined, linked and/or fastened thereto. For example, accessory port 148 may be threaded or include rotation locking grooves for receiving and retaining the accessory. In addition, accessory port 148 may include a sealing member 154 therein. Sealing member 154 may include any means for maintaining a closed circuit within respiratory valve apparatus 100 when accessory port 148 is or is not in use, i.e., when an accessory such as a suction catheter, bronchoscope, or drug delivery catheter is or is not being used. For example, sealing member 154 may include, for example, a dome valve, a duck-billed valve, a septum, o-ring, or combinations thereof. In some embodiments, sealing member 154 may include a flexible orifice or resealable entry. In further embodiments, sealing member 154 may be closed with a cap of resilient material having diametrical cuts forming openable flaps. Endotracheal tube connection port 150 (also known as a patient port) may be sized and shaped for receiving an endotracheal tube (not shown) being engaged, connected, attached, joined, linked and/or fastened thereto. For example, endotracheal tube connection port 150 may be threaded or include rotation locking grooves (not shown) for receiving and retaining the endotracheal tube. However, any conventional means may be used for receiving and retaining the endotracheal tube within or on endotracheal tube connection port 150. The endotracheal tube may be at least partially disposed within a patient (not shown), e.g., within a trachea of the patient.

Connection member 152 may include any means for matingly engaging with connection members 132 one of third end 126 or fourth end 128 of housing 102 opposite of conduit 136. Connection member 152 may include, for example, a flange, rib, rim, void, swivel connector, female connection member, and/or a male connection member. For example, where connection member 132 includes a male connection member, connection member 152 may include a female connection member. Connection members 152, 142 may matingly engage, connect, attach, join, link and/or fasten such that conduit 144 is in fluid communication with housing 102. While conduit 144 is shown as being matingly engaged with third end 128 of housing 102, it is to be understood that conduit 144 may instead matingly engage with fourth end 126. Connection members 152, 142 may allow for ergonomic positioning of conduit 144 relative to housing 102 thereby aiding in the use of accessory port 148 and endotracheal tube connection port 150. For example, connection members 132, 152 may engage such that connection members 132, 152 allow 360° rotation of conduit 144 to prevent kinking, twisting, or tangling of the artificial airway circuit.

As shown in FIGS. 1-2, conduit 144 may be substantially T-shaped such that accessory port 148 may be substantially aligned with and in fluid communication with endotracheal tube connection port 150. That is, accessory port 148 may be directly in-line with endotracheal tube connection port 150. In another embodiment, conduit 144 may be substantially L-shaped such that endotracheal tube connection port 150 and ventilator connection port 140 are in substantial alignment.

In some embodiments, respiratory valve apparatus 100 may also include another accessory port 158. Accessory port 158 may be optional and can include, e.g., an injection port or saline port when e.g., a suction catheter is used in connection with accessory port 148. Accessory port 158 may be sized and shaped for receiving another accessory such as a saline tube (not shown) being engaged, connected, attached, joined, linked and/or fastened thereto.

Figure 3:
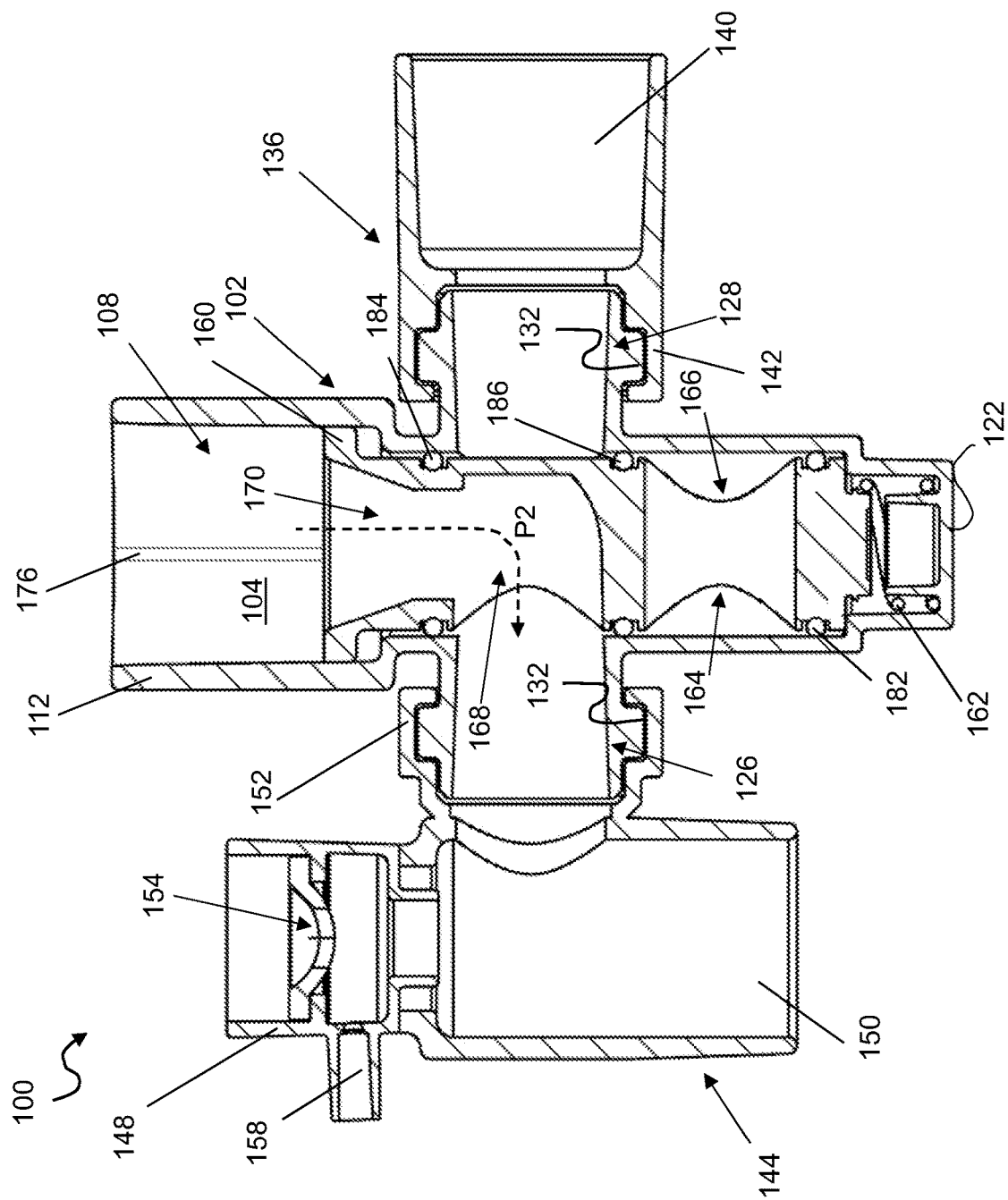
FIG. 3 shows a cross section of the respiratory valve apparatus in a second configuration including the piston in a second position thereby creating a second fluid pathway between the patient and a manual resuscitator or ambu-bag.

Referring now to FIG. 2-3, piston assembly 108 may include a piston 160 and a spring 162. As will be described herein, piston assembly 108 can allow two alternate air pathways passing through piston 160, and in turn respiratory valve apparatus 100, depending upon the position of piston 160. In addition to other benefits, piston assembly 108 minimizes dead space within respiratory valve apparatus 100, that in turn helps to maintain positive-end pressure, reduces the risk of the patient rebreathing $CO_2$ during ventilation, and reduces moisture buildup within respiratory valve apparatus 100. Piston assembly 108 may be disposed within inner chamber 104 of housing 102 and extend substantially along line B (FIG. 1). That is, piston assembly 108 may be disposed within housing 102 such that piston assembly 108 extends within inner chamber 104 between first end 116 having resuscitation bag connection port 112 and second, closed end 122. As shown in FIG. 2-3, spring 162 may be disposed between piston 160 and second end 122 of housing 102, while piston 160 may extend at least partially within resuscitation bag connection port 112 when spring 162 is in a non-compressed state. Piston assembly 108, or more specifically, piston 160 may be substantially cylindrical in shape and may include two distinct airflow passageways therein.

Figure 4:
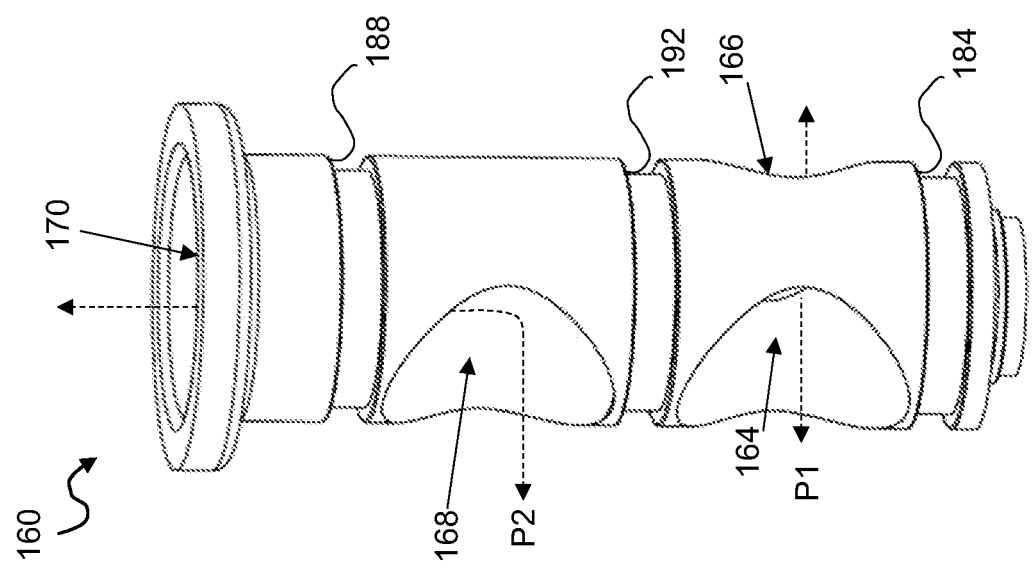
FIG. 4 shows a perspective side view of the piston according to an embodiment of the disclosure as described herein.

FIG. 4 shows an enlarged perspective view of piston 160. Referring now to FIG. 4 together with FIGS. 2-3, piston 160 may include a first opening 164 and a second opening 166 defining a first passageway (designated by dotted line arrows P1 (FIG. 2)). First passageway P1 may provide a first flow pathway between endotracheal tube connection port 150 (FIGS. 2-3) and ventilator connection port 140 (FIGS. 2-3) when piston 160 is in a first position, or when spring 162 is in a non-compressed state (FIG. 2). First passageway P1 may extend normal to a longitudinal axis of piston 160. Piston 160 may include a third opening 168 and a fourth opening 170 defining a second passageway (designated by dotted line arrows P2 (FIG. 3)). Second passageway P2 may extend both normal and parallel to the longitudinal axis of piston 160. Second passageway P2 may provide a second flow pathway between endotracheal tube connection port 150 and resuscitation bag connection port 112 (FIGS. 2-3) when in a second position, or when spring 162 is compressed (FIG. 3).

Referring only now to FIGS. 2-3, spring 162 may include, e.g., a compression spring. Spring 162 is to be used to securely move piston 160 thereby controlling the airflow from a ventilator (not shown) positioned at or within ventilator connection port 140 to the resuscitation bag positioned at or within resuscitation bag connection port 112, such as when the resuscitation bag is coupled to respiratory valve apparatus 100. Spring 162 may bias piston 160 in the first position thereby defining first flow pathway P1. Spring 162 may be attached to, e.g., via an adhesive an end of piston 160 that is disposed furthest from resuscitation bag connection port 112. However, spring 162 may be attached to piston 160 via any other reasonable means without departing from aspects of the disclosure, and may even merely rest against or contact piston 160 without being formally attached thereto.

Figure 5:
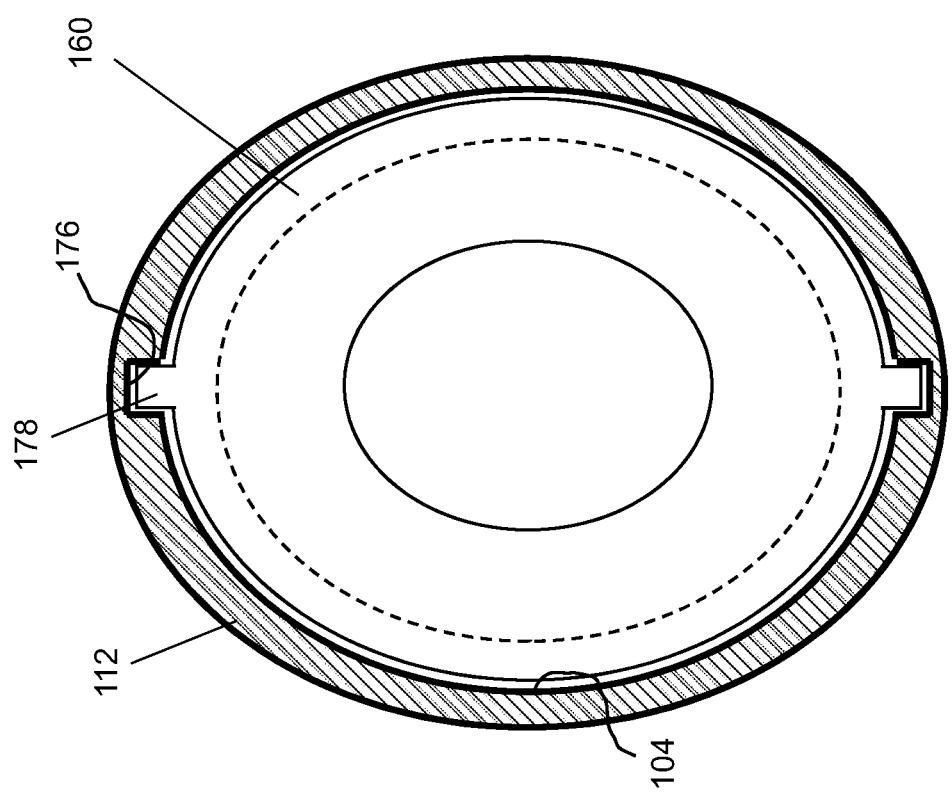
FIG. 5 shows a top-down view of the housing the respiratory valve apparatus including the resuscitation bag port having the piston therein.

Piston 160 may be retained within optional rotational locking grooves 176 (FIGS. 1 and 5), e.g., at least two grooves. Rotational locking grooves 176 may be formed within internal walls of housing 102. Rotational locking grooves 176 may matingly engage with locking tabs 178 (FIG. 5) on an external wall of at least a portion of piston 160, e.g., a portion of piston 160 that is at least partially disposed within resuscitation bag connection port 112 when respiratory valve apparatus 100 is in the first position (FIG. 2). Piston 160 can be moved within rotational locking grooves 176 between positions that affect the flow of air, i.e., up and down on the pages including FIGS. 2 and 3. Rotational locking grooves 176 may prevent piston 160 from rotating about the longitudinal axis of piston 160 within housing 102. This ensures proper alignment of flow pathways P1, P2 through piston 160 to line up with chambers in housing 102.

First and second flow pathways P1, P2 provided by piston 160 can be sealed in some embodiments. That is respiratory valve apparatus 100 can include one or more optional seals as may be necessary. For example, respiratory valve apparatus 100 can include a first seal 182 at a first end of piston 160, a second seal 184 at a second end of piston 160, and a third seal 186 positioned along the length of piston 160 between first and second ends of piston 160. More specifically, first seal 182 may be disposed at an end of piston 160 nearest spring 162 (FIGS. 2-3) or closed end 122 of housing 102. Second seal 186 may be disposed at an end of piston 160 furthest from spring 162 and closed end 122 of housing 102. Further, third seal 190 may be disposed at a position between openings 164, 166 defining first passageway P1 (FIG. 2) and openings 168, 170 defining second passageway P2 (FIG. 3) so that passageways P1, P2 are sealed off from one another. Additionally, first seal 182, second seal 184, and third seal 186 can be configured to assist with directing fluid or air flow through housing 102. First seal 182 and third seal 186 can assist with directing fluid or air flow through first flow pathway P1. Second seal 184 and third seal 186 can assist with directing fluid or air flow through second flow pathway P2. Each of first seal 182, second seal 184, and third seal 186 can include any type of seal for maintaining a closed circuit and assisting with directing fluid or air flow within pathways P1, P2. For example, seals 182, 184, 186 may include an o-ring, u-ring, v-ring, lip, double lip, cord ring, piston seal, rod seal, flange, chevron, wiper, etc. Seals 182, 184, 186 may be optionally positioned within seal grooves 188, 190, 192 (FIG. 4) within piston 160. Seal grooves 188, 190, 192 may be formed in and extend at least partially around an external surface of piston 160. Seal grooves 188, 190, 192 may be sized and shaped to house seals 182, 184, 186 such that passageways P1, P2 (FIGS. 2-3) are substantially sealed off from one another. While three seals and three seal grooves are shown, it is to be understood that any number of optional seals or seal grooves can be included without departing from aspects of the disclosure as described herein.

FIGS. 2-3 show respiratory valve apparatus 100 including piston assembly 108 in two possible positions during use. FIG. 2 shows respiratory valve apparatus 100 when piston assembly 108 is in a first portion, i.e., when no resuscitation bag is placed into/onto resuscitation bag connection port 112. As shown in FIG. 2, resuscitation bag connection port 112 is closed when piston 160 is in the first position thereby preventing flow through resuscitation bag connection port 112. Spring 162 biases piston 160 in the first position thereby creating the first flow pathway P1 to ventilator connection port 140. FIG. 3 shows respiratory valve apparatus 100 when piston assembly 108 is in a second position, i.e., when a resuscitation bag is placed into/onto resuscitation bag connection port 112. As shown in FIG. 3, ventilator connection port 140 is closed when piston 160 is in the second position thereby preventing flow through ventilator connection port 140. Compression of spring 162 places piston 160 in the second position thereby creating the second flow pathway P2 to resuscitation bag connection port 112. Once resuscitation bag is placed into/onto resuscitation bag connection port 112, piston 160 is actuated and spring 162 is compressed. During actuation of piston 160 (or compression of spring 162), piston 160 is forced in a direction toward second, closed end 122 of housing 102 which acts as a spring seat or stop for spring 162. In some embodiments, internal walls of housing 102 of resuscitation bag connection port 112 can be sloped to provide frictional forces along the wall of resuscitation bag connection port 112 as piston 160 reaches appropriate displacement thereby locking the resuscitation bag, and subsequently piston 160, in position for flow channels of endotracheal tube connection port 150 and resuscitation bag connection port 112 to become in fluid communication with one another. When the resuscitation bag is removed from resuscitation bag connection port 112, piston 160 is returned to a resting position and spring 162 is expanded. Air can then pass through ventilator pathway for mechanical ventilation of the patient (see FIG. 2).

Figure 6:
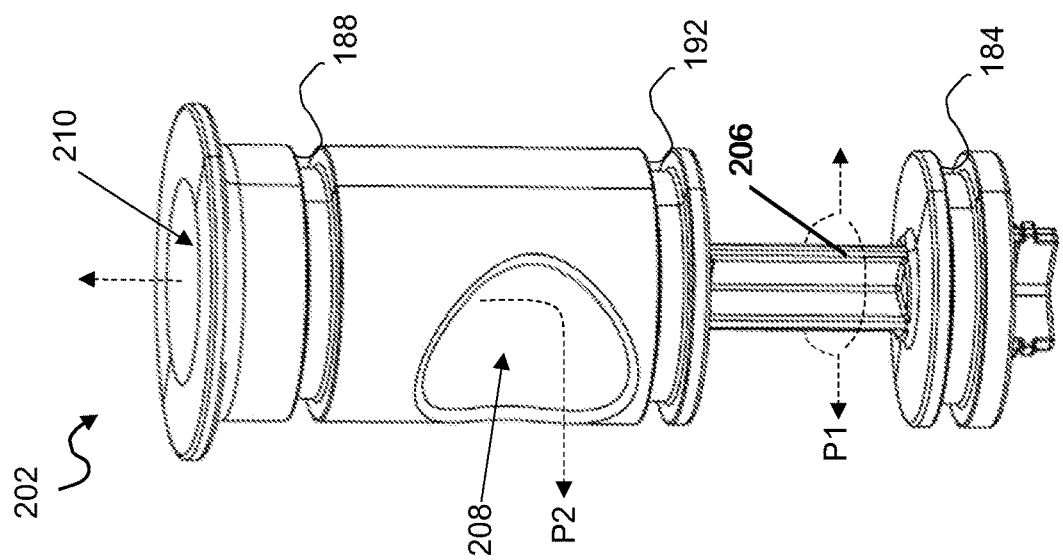
FIG. 6 shows a perspective side view of the piston according to another embodiment of the disclosure as described herein.

FIG. 6 shows a perspective view of a piston 202 that can be used with respiratory valve apparatus 100 according to another embodiment of the disclosure. Unlike piston 160, piston 202 does not include openings 164, 166. Rather, piston 202 includes a pillar 206 that is sized and shaped to allow air or fluid to pass through piston by passing around pillar 206 thereby defining first passageway P1. Like piston 160, piston 202 includes openings 208, 210 defining second passageway P2 as was described relative to FIGS. 1-2.

Figure 7:
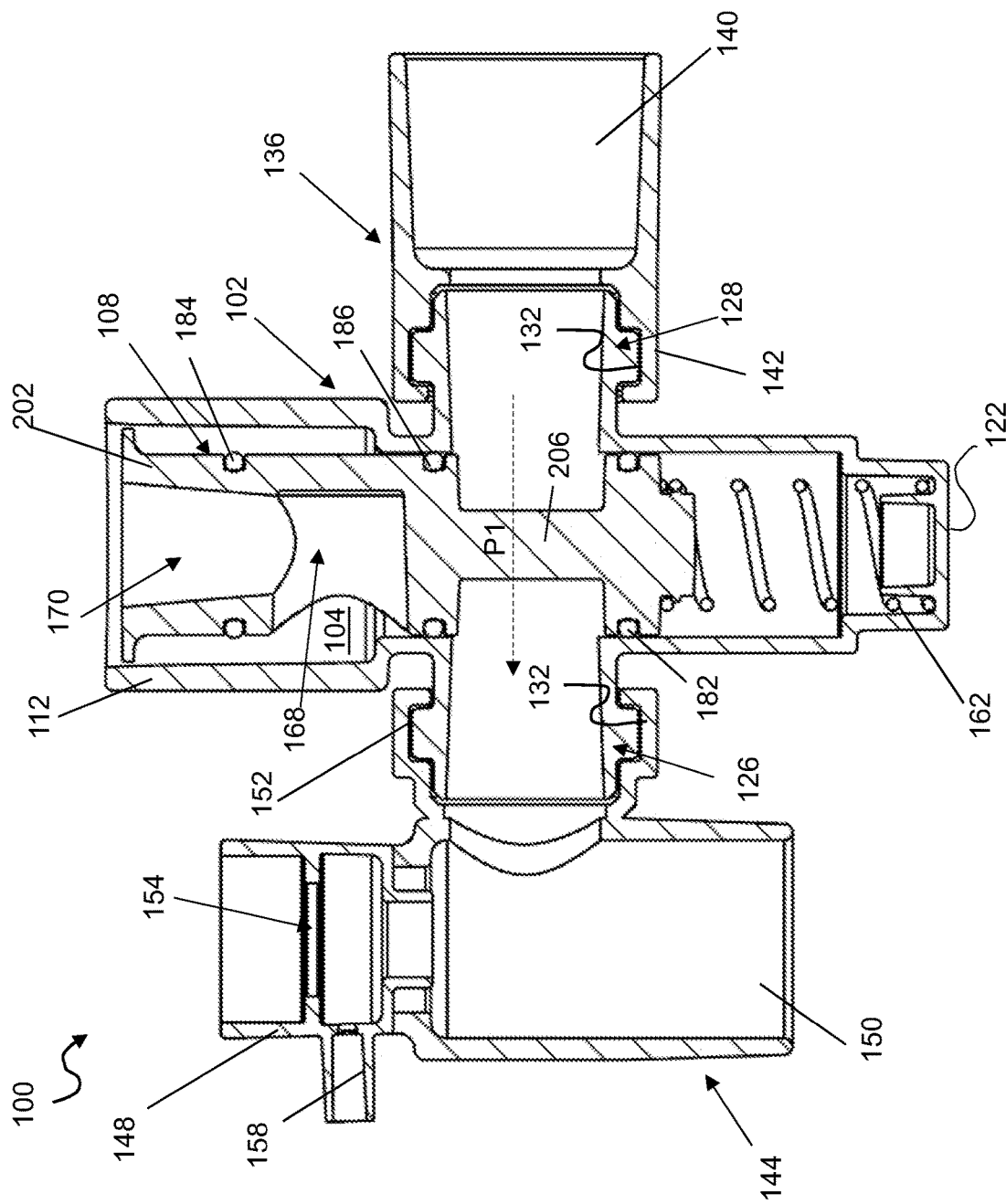
FIG. 7 shows a cross-section of the respiratory valve apparatus according to another embodiment of the disclosure in a first configuration including the piston of FIG. 6 in a first position thereby creating a first fluid pathway between a patient and a ventilator.
Figure 8:
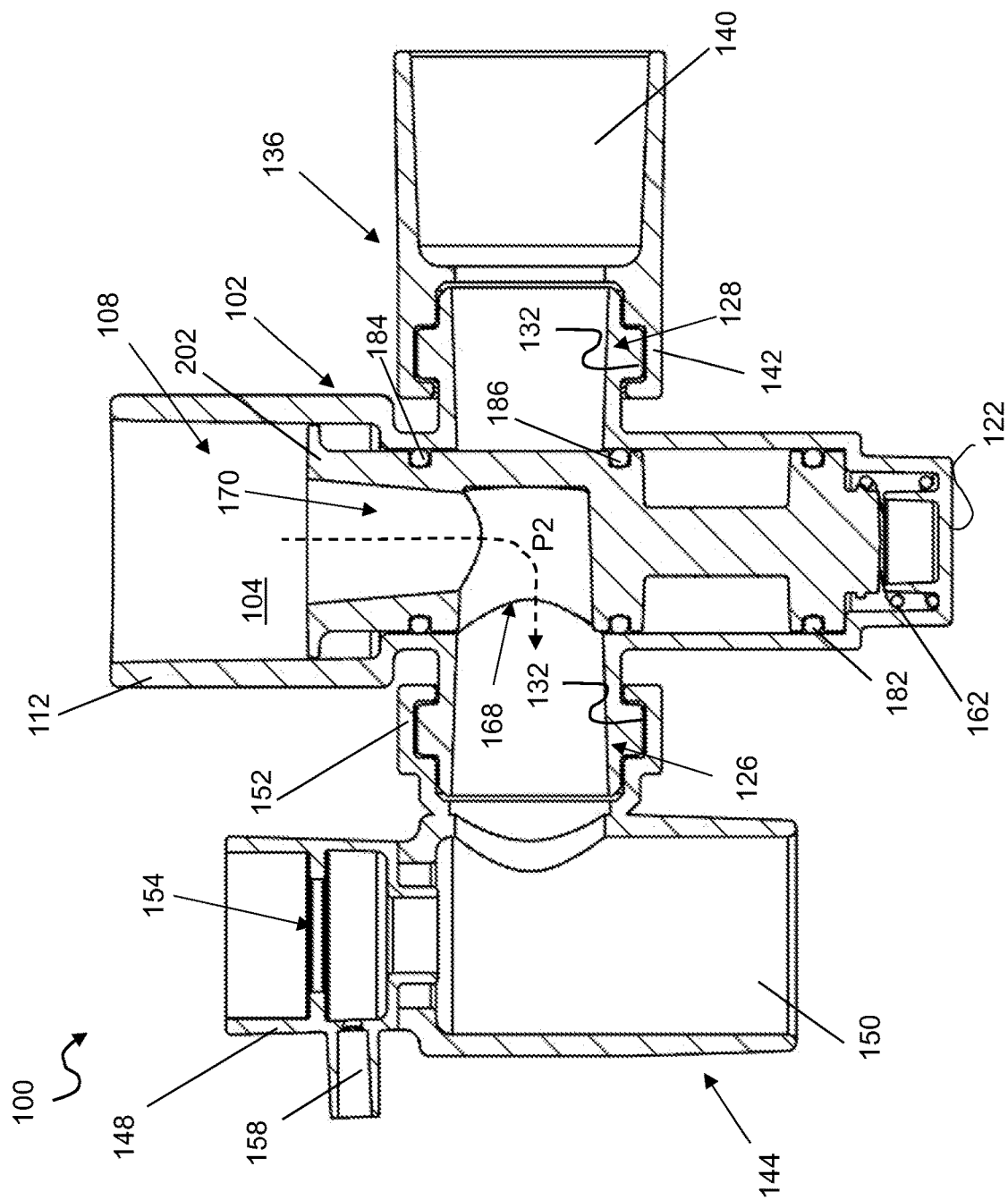
FIG. 8 shows a cross-section of the respiratory valve apparatus according to another embodiment of the disclosure in a second configuration including the piston of FIG. 6 in a second position thereby creating a second fluid pathway between the patient and a manual resuscitator or ambu-bag.

FIGS. 7-8 show respiratory valve apparatus 100 including piston assembly 108 having piston 202 in two possible positions during use. FIG. 7 shows respiratory valve apparatus 100 when piston assembly 108 is in a first portion, i.e., when no resuscitation bag is placed into/onto resuscitation bag connection port 112. As shown in FIG. 7, resuscitation bag connection port 112 is closed when piston 202 is in the first position thereby preventing flow through resuscitation bag connection port 112. Spring 162 biases piston 202 in the first position thereby creating the first flow pathway P1 to ventilator connection port 140. FIG. 8 shows respiratory valve apparatus 100 when piston assembly 108 is in a second position, i.e., when a resuscitation bag is placed into/onto resuscitation bag connection port 112. As shown in FIG. 8, ventilator connection port 140 is closed when piston 202 is in the second position thereby preventing flow through ventilator connection port 140. Compression of spring 162 places piston 202 in the second position thereby creating the second flow pathway P2 to resuscitation bag connection port 112. Once the resuscitation bag is placed into/onto resuscitation bag connection port 112, piston 202 is actuated and spring 162 is compressed. During actuation of piston 202 (or compression of spring 162), piston 202 is forced in a direction toward second, closed end 122 of housing 102 which acts as a spring seat or stop for spring 162. In some embodiments, internal walls of housing 102 of resuscitation bag connection port 112 can be sloped to provide frictional forces along the wall of resuscitation bag connection port 112 as piston 202 reaches appropriate displacement thereby locking the resuscitation bag, and subsequently piston 202, in position for flow channels of endotracheal tube connection port 150 and ventilator connection port 140 to become in fluid communication with one another. When the resuscitation bag is removed from resuscitation bag connection port 112, piston 202 is returned to a resting position (or what is shown in FIG. 7) and spring 162 is expanded. Air or fluid can then pass through respirator pathway for mechanical ventilation of the patient (see FIG. 8).

Figure 9:
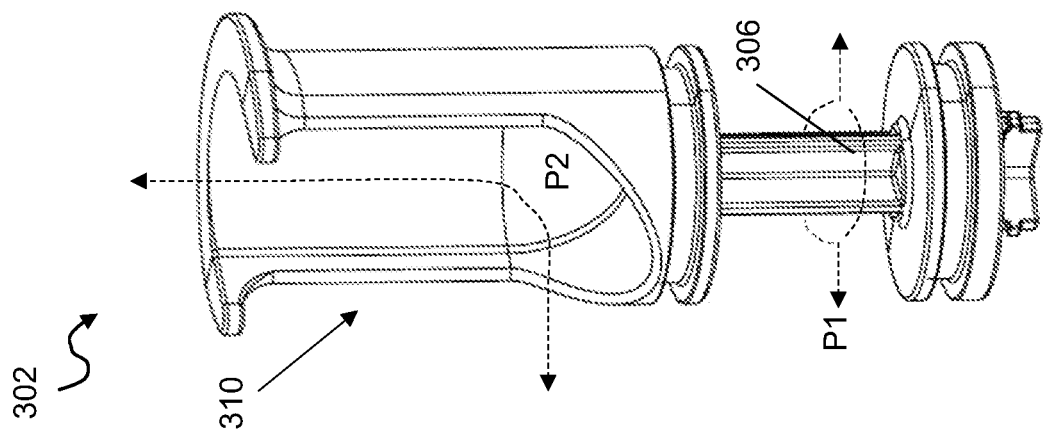
FIG. 9 shows a perspective side view of the piston according to another embodiment of the disclosure as described herein.

FIG. 9 shows a perspective view of a piston 302 that can be used with respiratory valve apparatus 100 according to another embodiment of the disclosure. Unlike piston 160, and like piston 202, piston 302 does not include openings 164, 166. Rather, piston 302 includes a pillar 306 that is sized and shaped to allow air or fluid to pass through piston 302 by passing around pillar 306 thereby defining first passageway P1. Additionally, unlike both piston 160 and piston 202, piston 302 does not include two openings to define second passageway P2 as was described relative to FIGS. 1-2 and 7-8. Rather, a portion of the sidewall of the piston 302 at an end nearest resuscitation bag connection port 112 is removed and is open continuously through to a surface of piston 302 nearest resuscitation bag connection port 112 (or an upper surface as shown on the page containing FIG. 9). That is, an opening 310 may be disposed through a sidewall of piston 160. Opening 310 may be continuous through to a surface of piston 160 that is furthest from spring 162 (FIGS. 2-3 and 7-8).

While not shown herein together with respiratory valve apparatus 100, it is to be understood that piston 302 operates in much of the same way as piston 160, 202 and is not shown herein for brevity. Like pistons 160, 202, piston 302 may be actuated by use or connection of a resuscitation bag onto/into resuscitation bag connection port 112 (FIGS. 1-3 and 7-8) and compression of spring 162 (FIGS. 2-3 and 7-8) such that piston 302 causes alternating of the flow between passageway P1 and passageway P2.

Respiratory valve apparatus 100 described herein can provide at least the following: improved transition between mechanical ventilation and manual ventilation; reduced dead space volume within the piston thereby reducing both the risk of losing positive-end pressure within the lungs of the patient and reducing the risk of contamination within the piston (e.g., reduction of infection risk for patient); improved ability to conduct ventilator weaning studies on the patient without risking opening the circuit and removing the patient from mechanical ventilation too early in recovery. Respiratory valve apparatus 100 can be substantially T-shaped, x-shaped, Y-shaped, or t-shaped. Respiratory valve apparatus 100 can include or be a part of a kit having a resuscitation bag adapted to securely connect with the resuscitation bag connection port, an endotracheal tube adapted to securely connect with the endotracheal connection port.

It is to be understood that while housing 102 and conduits 136, 144 have been described as separate pieces that may matingly engage, it is to be understood that housing 102 and conduits 136, 144 may be formed as one integral piece or part in other embodiments. Housing 102 and conduits 136, 144 may be composed of any now know or later developed material used for respiratory or medical valves such as, for example, a plastic, a metal, a polymer, polypropylene, medical grade silicone, etc. Housing 102 may be substantially t-shaped, x-shaped, or any other shape that is able to maintain a closed circuit and can define pathways P1, P2 together with piston assembly 108. Respiratory valve apparatus 100 may be formed by injection molding, rotational molding, blow molding, compression molding, 3D printing or additive manufacturing, machining, or any now known or later developed method for forming respiratory or medical valves. Pistons 160, 202, 302 may be composed of any now know or later developed material used for respiratory or medical pistons such as, for example, a plastic, a metal, a composite, a polymer, etc. Pistons 160, 202, 302 may be formed by injection molding, rotational molding, blow molding, compression molding, 3D printing or additive manufacturing, machining, or any now known or later developed method for forming respiratory or medical pistons.

Additionally, while various embodiments of the piston (e.g., piston 160, 202, 302) have been shown and described herein, it is to be understood that any piston that can allow at least two passageways for fluidly connecting an endotracheal tube port to a ventilator connection port and the endotracheal tube port to a resuscitation bag port (e.g., passageways P1, P2) can be used without departing from aspects of the disclosure. That is, the respiratory valve apparatus can be used together with any piston that is capable of switching from mechanical ventilation to manual ventilation (e.g., via a resuscitation bag) without opening of the ventilation circuit; allowing the conduction of lung measurement studies without opening the ventilator circuit; and switching from a ventilator to a resuscitation bag as the resuscitation bag is placed on or in connection with the resuscitation bag port.

Figure 10:
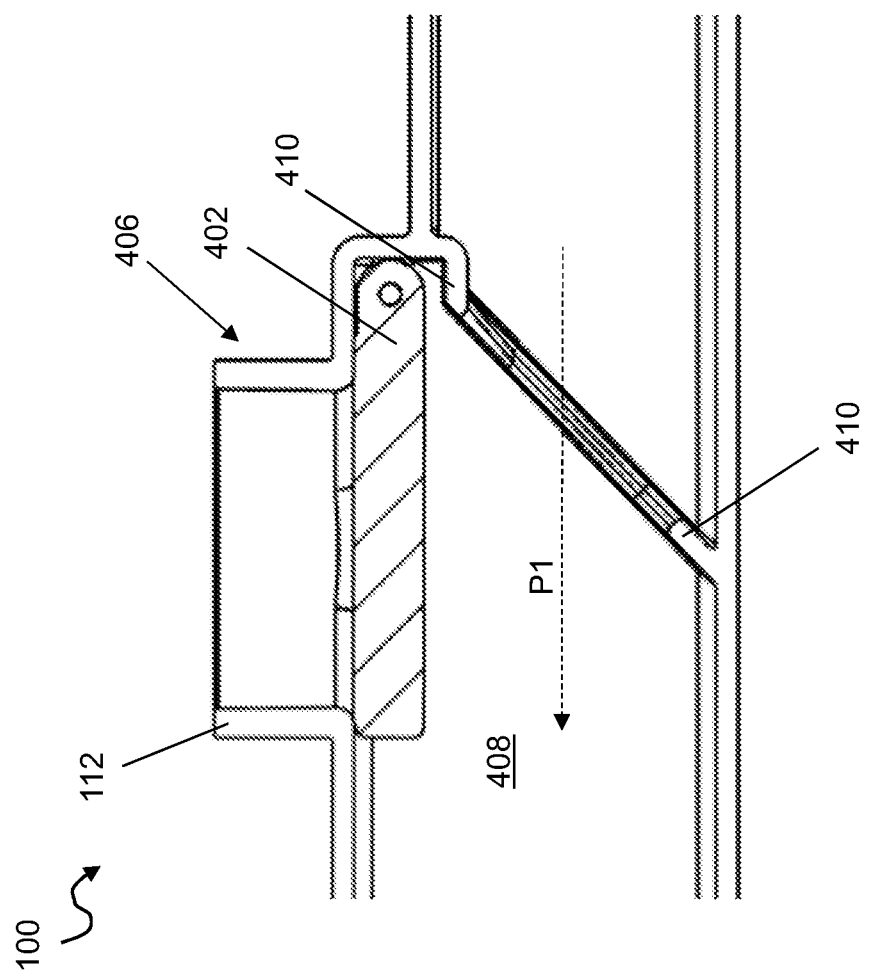
FIG. 10 shows an enlarged cross-section of a portion of the respiratory valve apparatus according to another embodiment of the disclosure in a first configuration including a lever member thereby creating a first fluid pathway between the patient and a ventilator.
Figure 11:
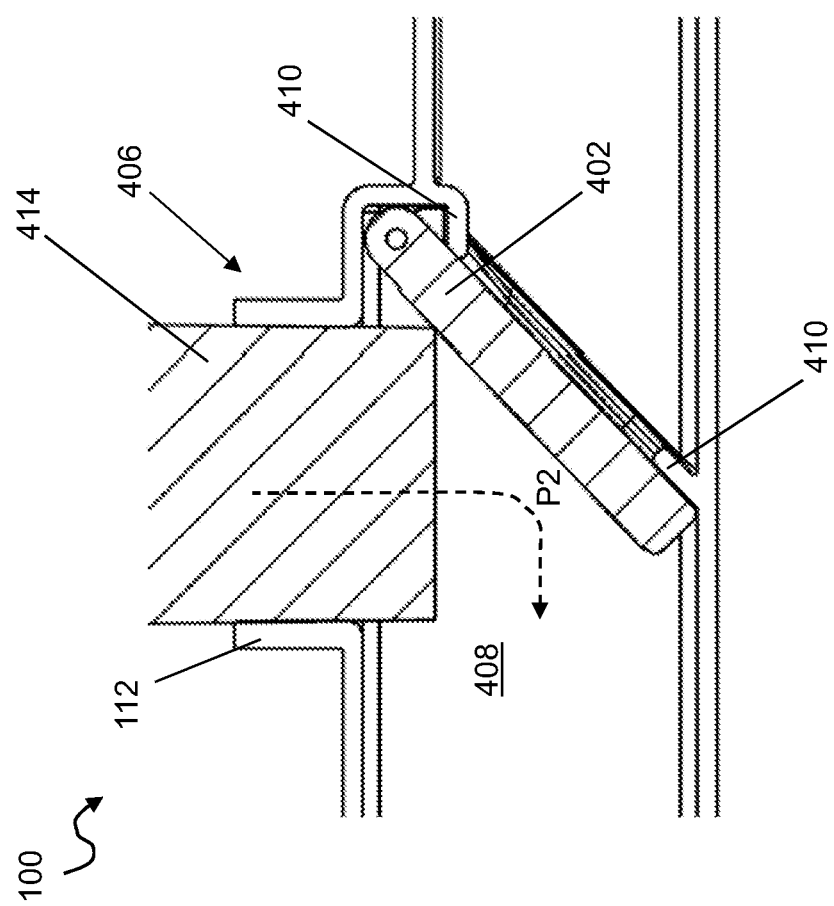
FIG. 11 shows an enlarged cross-section of a portion of the respiratory valve apparatus according to another embodiment of the disclosure in a second configuration including a lever member thereby creating a second fluid pathway between the patient and the manual resuscitator or ambu-bag.

FIGS. 10-11 show an enlarged cross-section of a portion of respiratory valve apparatus 100 according to another embodiment of the disclosure. In this embodiment, the piston, e.g., piston 160 (FIGS. 2-4), 202 (FIGS. 6-7), 302 (FIG. 9), of the previous embodiments is replaced with a lever member 402. FIG. 10 shows respiratory valve apparatus 100 including lever member 402 in a first position defining a first passageway P1 between endotracheal tube connection port 150 (FIGS. 1-3 and 7-8) and ventilator connection port 140 (FIGS. 1-3 and 7-8). FIG. 11 shows respiratory valve apparatus 100 including lever member 402 in a second position defining a second passageway P2 between endotracheal tube connection portion 150 and resuscitation bag connection port 112.

In this embodiment, respiratory valve apparatus 100 may include housing 406 having an inner chamber 408 therein. Housing 406 may differ from housing 102 (FIGS. 1-3 and 7-8) in that housing 406 is substantially T-shaped and does not require a spring seat. Rather, housing 406 may include at least one projection 410 therein for supporting and positioning lever member 402. Projection 410 may include, for example, a lip or a rib. Projection 410 may be disposed or positioned within inner chamber 408 such that projection 410 aids lever member 402 in sealing passageways P1, P2 and may act as or provide a seat or stop for lever member 402. Projection 410 may be integrally formed within housing 402 and/or may be a separate member attached therein. Projection 410 may include a single unitary body that extends circumferentially about inner chamber 408 within housing 406. Projection 410 may be angled about inner chamber 408 at any angle sufficient to aid lever member 402 in sealing in the second position (FIG. 11). In another embodiment, projection 410 may include separate projections circumferentially spaced about inner chamber 408. It is to be understood that projection 410 may include any now known or later developed means for aiding in sealing and positioning of lever member 402 within inner chamber 408.

Lever member 402 may be disposed within the inner chamber 408. Lever member 402 may include any type of bar, rod, flap, etc. Lever member 402 may be any shape or type of member for substantially sealing passageways P1, P2. As shown in FIGS. 10-11, lever member 402 may be pivotable from a first position (FIG. 10) to a second position (FIG. 11). That is, lever member 402 may be pivotably attached to housing 406 within inner chamber 408. Lever member 402 may be biased in the first position thereby such that when there is no resuscitation bag disposed within resuscitation bag connection port 112, lever member 402 defines first passageway P1 between endotracheal tube connection port 150 and ventilator connection port 140. Additionally, resuscitation bag connection port 112 is closed when lever member 402 is in the first position thereby preventing flow through resuscitation bag connection port 140. Lever member 402 may be biased, for example, via the material properties of lever member 402, a flat spring, a compression spring, a torsion spring, or any other now known or later developed means for biasing lever member 402 in the first position thereby preventing flow through resuscitation bag connection port 140. The biasing of lever member 402 in the first position may be assisted by the fluid pressure (air pressure) of a ventilator (not shown) disposed within or on ventilator connection port 140 (FIGS. 1-3 and 7-8).

Lever member 402 may be pivotable to the second position thereby defining a second passageway P2 between the endotracheal tube connection port 150 and resuscitation bag connection port 112. That is, lever member 402 may be actuated, or may switch to the second position, upon insertion of a resuscitation bag 414 (FIG. 11) within resuscitation bar port 112. More specifically, as shown in FIG. 11, upon insertion of resuscitation bag 414, resuscitation bag 414 may contact lever member 402 and force lever member 402 in a direction toward projections 410 to actuate lever member 402 to actuate from the first position to the second position such that ventilator connection port 140 is closed and resuscitation bag connection port 112 is open. That is, ventilator connection port is closed when lever member 402 is in the second position thereby preventing flow through ventilator connection port 140. Lever member 402 may be held in place in the second position so long as resuscitation bag 414 remains disposed within resuscitation bag connection port 112. In addition, the fluid pressure (air pressure) of resuscitation bag 414 may provide additional force to lever member 402 to maintain lever member 402 in the second position and aid in sealing second passageway P2 (FIG. 11). Once resuscitation bag 414 is removed from resuscitation bag connection port 112 lever member 402 may be returned to the first position (FIG. 10). That is, once resuscitation bag 414 is removed and no longer applies a force to lever member 402, lever member 402 will return to the first position since lever member 402 is biased in first position.

The disclosure is also directed to a method. The method may include providing respiratory valve apparatus 100 according to at least one of the embodiments described herein and placing a resuscitation bag (e.g., resuscitation bag 414 (FIG. 11) onto resuscitation bag connection port 112 thereby actuating piston assembly 108 (FIGS. 2-4 and 6-9) or lever member 402 (FIGS. 10-11) such that first passageway P1 (i.e., the passageway between endotracheal tube connection port 150 between ventilator connection port 140) closes the second passageway P2 (i.e., the passageway between endotracheal tube connection port 150 and resuscitation bag connection port 112) opens. In one embodiment, the actuating of piston assembly 108 may include compressing spring 162 disposed within inner chamber 104 of housing 102. Further, once resuscitation bag is no longer needed or in use, the method may include removing the resuscitation bag from resuscitation bag connection port 112 thereby actuating piston assembly 108 such that first passageway P1 opens and second passageway P2 closes. The actuating of piston assembly 108 such that first passageway P1 opens and second passageway P2 closes may include expanding spring 162 disposed within inner chamber 104 of housing 102. In another embodiment, the actuating of lever member 402 may include forcing or causing lever member 402 to contact projection 410. The placing of the resuscitation bag onto resuscitation bag connection port 112 and the removing of the resuscitation bag from resuscitation bag connection port 112 may be performed such that respiratory valve apparatus 100 remains a closed circuit during operation.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The particular embodiments disclosed above are illustrative only, as the disclosure may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the disclosure. Note that the use of terms, such as "first," "second," "third" or "fourth" to describe various processes or structures in this specification and in the attached claims is only used as a shorthand reference to such steps/structures and does not necessarily imply that such steps/structures are performed/formed in that ordered sequence. Of course, depending upon the exact claim language, an ordered sequence of such processes may or may not be required. Accordingly, the protection sought herein is as set forth in the claims below.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A respiratory valve apparatus comprising:
   a housing having an inner chamber, an endotracheal tube connection port, a ventilator connection port, and a resuscitation bag connection port; and
   a piston assembly positioned within the inner chamber and including a piston having a first passageway and a distinct second passageway through the piston, wherein the first passageway provides a first flow pathway between the endotracheal tube connection port and the ventilator connection port when the piston is in a first position, and wherein the second passageway provides a second flow pathway between the endotracheal tube connection port and the resuscitation bag connection port when in a second position, wherein the piston defines a first opening and a second opening defining the first passageway through the piston and a third opening and a fourth opening defining the second passageway through the piston.

2. The respiratory valve apparatus of claim 1, wherein the resuscitation bag connection port is closed when the piston is in the first position thereby preventing flow through the resuscitation bag connection port.

3. The respiratory valve apparatus of claim 1, wherein the ventilator connection port is closed when the piston is in the second position thereby preventing flow through the ventilator connection port.

4. The respiratory valve apparatus of claim 1, wherein the piston assembly includes a spring that biases the piston in the first position thereby creating the first flow pathway.

5. The respiratory valve apparatus of claim 4, wherein compression of the spring places the piston in the second position thereby creating the second flow pathway.

6. The respiratory valve of claim 1, wherein the piston is substantially cylindrical in shape.

7. The respiratory valve apparatus of claim 1, wherein the first passageway extends normal to a longitudinal axis of the piston and the second passageway extends both normal and parallel to the longitudinal axis of the piston.

8. The respiratory valve apparatus of claim 1, wherein the piston includes a first seal at a first end of the piston, a second seal at a second end of the piston, and a third seal positioned along the length of the piston between the first and the second end, the third seal being parallel to the first seal and the second seal, wherein the first, second, and third seals are configured to assist with directing fluid flow through the housing.

9. The respiratory valve apparatus of claim 8, wherein the first seal and third seal assist with directing fluid flow through the first flow passageway.

10. The respiratory valve apparatus of claim 8, wherein the second seal and third seal assist with directing fluid flow through the second flow passageway.

11. The respiratory valve apparatus of claim 8, wherein each of the first seal, second seal, and third seal include an o-ring, u-ring, v-ring, lip, double lip, cord ring, piston seal, rod seal, flange, chevron, or wiper.

12. The respiratory valve apparatus of claim 1, which further includes a kit having a resuscitation bag adapted to securely connect with the resuscitation bag connection port, and an endotracheal tube adapted to securely connect with the endotracheal connection port.

13. The respiratory valve apparatus of claim 1, wherein the housing is generally T shaped where the ventilator connection port and the endotracheal connection port are in alignment with one another and the resuscitator bag connection port is positioned perpendicular to the ventilator connection port and the endotracheal connection port.

14. The respiratory valve apparatus of claim 1, wherein the piston includes a pillar that is sized and shaped to allow air or fluid to pass around it thereby defining first passageway.

15. The respiratory valve apparatus of claim 14, wherein the piston further includes an opening through a sidewall of the piston, the opening being continuous through the sidewall of the piston to a surface of the piston that is furthest from a spring, wherein the spring directly abuts the piston.

16. A respiratory valve apparatus comprising:
   a housing having an inner chamber, an endotracheal tube connection port, a ventilator connection port, and a resuscitation bag connection port; and
   a pivotable lever member disposed within the inner chamber, the pivotable lever member being biased in a first position thereby defining a first passageway between the endotracheal tube connection port and the ventilator connection port, and wherein the pivotable lever member is pivotable to a second position thereby defining a second passageway between the endotracheal tube connection port and the resuscitation bag connection port, wherein the pivotable lever member is configured to actuate between the first position and the second position by receiving or releasing a resuscitation bag by the resuscitation bag connection port.

17. The respiratory valve apparatus of claim 16, further comprising:
   a projection disposed within the inner chamber and providing a seat for the pivotable lever member.

18. The respiratory valve apparatus of claim 16, wherein the resuscitation bag connection port is closed when the pivotable lever member is in the first position thereby preventing flow through the resuscitation bag connection port.

19. The respiratory valve apparatus of claim 16, wherein the ventilator connection port is closed when the pivotable lever member is in the second position thereby preventing flow through the ventilator connection port.

20. The respiratory valve apparatus of claim 16, further comprising:
   a resuscitation bag disposed at the resuscitation bag connection port and at least partially within the inner chamber of the housing such that the resuscitation bag causes the pivotable lever member to actuate from the first position to the second position.

* * * * *